(12) United States Patent
Solomon et al.

(10) Patent No.: US 7,485,616 B2
(45) Date of Patent: Feb. 3, 2009

(54) METHODS OF INVESTIGATING, DIAGNOSING, AND TREATING AMYLOIDOSIS

(75) Inventors: Alan Solomon, Knoxville, TN (US); Jonathan Stuart Wall, Knoxville, TN (US); Rudi Hrncic, Knoxville, TN (US); Maria Schell, Knoxville, TN (US)

(73) Assignee: University of Tennessee Research Foundation, Knoxville, TN (US)

( * ) Notice: Subject to any disclaimer, the term of this patent is extended or adjusted under 35 U.S.C. 154(b) by 582 days.

(21) Appl. No.: 09/825,872

(22) Filed: Apr. 5, 2001

(65) Prior Publication Data

US 2002/0019335 A1 Feb. 14, 2002

Related U.S. Application Data

(60) Provisional application No. 60/194,684, filed on Apr. 5, 2000.

(51) Int. Cl.
*A61K 38/00* (2006.01)
*A61K 38/17* (2006.01)

(52) U.S. Cl. .............. 514/2; 514/12; 530/350; 530/387.1; 424/130.1; 424/9.1

(58) Field of Classification Search ............. 514/12, 514/8, 6, 2; 436/501, 503, 518, 86; 435/7.8, 435/7.9, 7.93, 23; 800/18, 12; 530/350, 530/395, 400, 387.1; 424/85.1, 9.1, 130.1
See application file for complete search history.

(56) References Cited

U.S. PATENT DOCUMENTS

| 4,828,563 | A | * | 5/1989 | Muller-Lierheim | 623/23.63 |
| 5,583,005 | A | * | 12/1996 | Nishimura et al. | 435/7.94 |
| 5,643,570 | A | * | 7/1997 | Theofan et al. | 424/134.1 |
| 5,750,106 | A | * | 5/1998 | Ostberg et al. | 424/142.1 |
| 6,875,434 | B1 | * | 4/2005 | Schenk | 424/184.1 |
| 2002/0019335 | A1 | * | 2/2002 | Solomon et al. | 514/2 |

FOREIGN PATENT DOCUMENTS

| WO | 91/16819 | | 11/1991 |
| WO | 95/12815 | | 5/1995 |
| WO | 95/31996 | | 11/1995 |
| WO | WO 96/25435 | * | 8/1996 |
| WO | 99/27944 | | 6/1999 |
| WO | 99/60024 | | 11/1999 |
| WO | 00/72876 A2 | | 12/2000 |

OTHER PUBLICATIONS

Helmuth, L.; "Further Progress on a β-Amyloid Vaccine"; Science, vol. 289, No. 5478, Jul. 21, 2000, pp. 349-496.
Schenk et al.; Immunication with amyyloid-β anntenuates Alzheimer-disease-like pathology in the PDAPP mouse, Nature, vol. 400, No. 6740, Jul. 8, 1999, pp. 173-177.

* cited by examiner

*Primary Examiner*—Chih-Min Kam
(74) *Attorney, Agent, or Firm*—Morgan, Lewis & Bockius LLP

(57) ABSTRACT

The present invention provides a therapeutic method for removing amyloid fibrils from a patient. The present invention also provides a transgenic animal that develops systemic AA amyloidosis within three weeks for use as a tool to investigate AA amyloidosis and to evaluate agents that may be potentially useful in preventing and treating amyloid-related disorders. Further, the present invention provides diagnostic assays for monitoring immunoglobulin light chain fibrillogenesis in real-time and for identification of the chemical nature of the protein in amyloid deposits which enables the determination of the type of amyloidosis for therapeutic and prognostic purposes.

19 Claims, 7 Drawing Sheets

Liver

Kidney

FIG. 3

AA- GFFSFIGEAFQGAGDMWRAYTDMKEAGWKDGDKYFHARGNYDAAQRGPGGVWAAEKIS

MT-I/hIL6- ---------------------------------------------------

MRI

CT

METHODS OF INVESTIGATING, DIAGNOSING, AND TREATING AMYLOIDOSIS

RELATED APPLICATION

This application claims the benefit of U.S. Provisional Application No. 60/194,684 filed Apr. 5, 2000, which is herein incorporated by reference in its entirety.

ACKNOWLEDGEMENT OF FEDERAL SUPPORT

The research and discoveries described herein were supported in part by U.S. Public Health Research Grant CA 10056 from the National Cancer Institute and National Science Foundation Grant BIR-94 08252.

TECHNICAL FIELD

The present invention relates to the development of methods and tools effective for treating and diagnosing amyloidosis. Specifically, the present invention relates to compositions and methods of removing amyloid fibrils from a patient to prevent aggregation of the fibrils and to transgenic animals useful for investigating amyloidosis and for identifying therapeutic agents for treating amyloidosis. The present invention also relates to investigating the fibrillogenesis of polypeptides and to methods of determining the chemical nature of the polypeptides in an amyloid deposit.

BACKGROUND OF INVENTION

Amyloidoses represent a spectrum of diseases characterized by the aggregation and deposition of amyloid. Amyloid is a generic term referring to abnormal extracellular and/or intracellular deposits of proteins as fibrils. Amyloid fibrils may be deposited in a variety of vital organs including brain, liver, heart, kidney, pancreas, nerve and other tissues as a consequence of certain inherited and acquired disorders such as Alzheimer's disease, multiple myeloma and related conditions, neuropathies (ATTR amyloidosis), cardiomyopathies, monoclonal plasma cell dyscrasias (AL amyloidosis), adult-onset diabetes, chronic inflammation (AA amyloidosis), aging, bovine spongiform encephalopathy (BSE), Creutzfeld-Jacob disease (CJD), and scrapie.

A. Characterization of Amyloid Proteins

Amyloid is not a uniform deposit and may be composed of unrelated proteins. Proteins that have been identified as capable of forming amyloid in human diseases include immunoglobulin light chains, serum amyloid A protein, $\beta$2-microglobulin, transthyretin, cystatin C variant, gelsolin, procalcitonin, PrP protein, amyloid $\beta$-protein, ApoA1, and lysozyme. Although these proteins are unrelated, the fibrils which they form have the following common biological properties: 1) they possess a $\beta$-pleated sheet secondary structure; 2) they are insoluble aggregates; 3) they exhibit green birefringence after Congo red staining; and 4) they possess a characteristic unbranching fibrillar structure when observed under an electron microscope.

B. Classification of Amyloidosis

Before the major proteins involved in amyloidosis were isolated, sequenced and identified, amyloid was classified based on clinical features into four categories: primary amyloid, secondary amyloid, familial amyloid, and isolated amyloid (U.S. Pat. No. 5,958,883). Primary amyloid is amyloid appearing de novo, without any preceding disorder. Secondary amyloid appears as complication of a previously existing disorder. Patients with rheumatoid arthritis, osteoarthritis, or ankylosing spondylitis can develop secondary amyloidosis as do patients with tuberculosis, lung abscesses, and osteomyelitis.

Familial form of amyloid is found in patients diagnosed with genetically inherited forms of amyloid. Several geographic populations have been identified with such forms of amyloid. One form of inherited amyloid is found in patients with Familial Mediterranean Fever. Sephardic Jews in Israel possess a genetic predisposition for Familial Mediterranean Fever. A second form is found in patients diagnosed with Familial Amyloidotic Polyneuropathy. Patients of three different nationalities, Swedish, Portuguese, and Japanese have been shown to possess a genetic predisposition referred to as Familial Amyloidotic Polyneuropathy.

Unlike the other three forms of amyloid, isolated amyloid only tends to involve a single organ system. Type II diabetic patients have isolated amyloid deposits in the pancreas restricted to the beta cells in the islets of Langerhans. A serious complication of long-term hemodialysis is amyloid deposited in the medial nerve and clinically associated with carpal tunnel syndrome. In Alzheimer's disease, amyloid deposition is restricted to the central nervous system (CNS). Similarly, in Down's syndrome patients, deposition of amyloid occurs in the brain when the patient reaches approximately 35 years of age.

Currently, amyloid is classified according to major protein type found associated with the disorder (U.S. Pat. No. 5,958, 883). The major proteins isolated and sequenced are AA amyloid, AL amyloid, transthyretin, $\beta$2-microglobulin, procalcitonin, $\beta$ amyloid protein or $\beta$/A4, and Prp protein.

AA amyloid is commonly found in a host of seemingly unrelated disorders including chronic inflammation, various forms of malignancy, and in Familial Mediterranean Fever. AA amyloid is also found in animal models which use daily repeated injections of pro-inflammatory stimulants such as casein or azocasein. In these animals, amyloid deposition is detected in the spleen, liver, and kidney within 7-10 days of the initial injections. The isolated AA amyloid protein is approximately 76 amino acids long and has a molecular weight of about 85 Kda. These 76 amino acids correspond to the amino terminal $\frac{2}{3}$s of the naturally occurring serum protein, serum amyloid A (SAA). SAA is an acute phase protein whose concentration increases by a thousand-fold within 24 hours during any inflammatory disorder. It is made by the liver, but current research has suggested that it is present in other tissues as well.

AL amyloid usually occurs secondary to multiple myeloma, or B-cell type malignancies, and other plasma cell dyscrasias. Not all patients with multiple myeloma develop AL amyloid; only 10 to 15% develop AL amyloid related clinical problems. AL amyloid is usually due to the deposition of the variable region of immunoglobulin light chains, either lambda or kappa chain, but the entire light chain may also be present. Due to the inherent amino acid sequence diversity seen in the variable region of the light chains, AL amyloid isolated from different patients differs in its amino acid sequence. However, within a single patient the sequence of the AL amyloid protein is constant regardless of the organ from which the amyloid is isolated.

Transthyretin (TTR) is another name for prealbumin. Prealbumin or TTR is the serum carrier of thyroxine, retinol binding protein, and retinoic acid. It is synthesized by the liver and consists of 127 amino acids. TTR forms amyloid deposits in patients with certain familial amyloid polyneuropathy (FAP). It has been determined that TTR found in the deposits has various amino acid substitutions compared to circulating transthyretin of normal individuals. Single amino acid substitutions have been identified at a number of positions within the molecule, including: 30, 33, 60, 77, 84, 111, and 122. These were identified in TTR molecules isolated from amyloid deposit of FAP patients. The most common substitution is a methionine for valine at position 30 of the molecule.

β2-Microglobulin is present in the amyloid deposits of patients having serious complications from long-term hemodialysis. It is also associated with disorders such as carpal tunnel syndrome, joint swelling, multiple spontaneous fractures, and radiolucency in the wrist and hip. β2-Microglobulin is a single polypeptide chain of 100 amino acid residues and has a molecular weight of about 11.8 Kda. It accumulates not only in the blood of uremic patients but also in the synovial fluid and in the tissues.

Procalcitonin is found in the amyloid deposits of endocrine tumors which secrete calcitonin. Medullary carcinoma of the thyroid is an example of such a tumor. The tumor is related to the C-type cells of the thyroid which normally secrete calcitonin.

β-Amyloid protein or β/A4 is deposited in the brains of patients with Alzheimer's disease as well as Down's syndrome patients over the age of 35. β-Amyloid protein has a molecular weight of 4.2 Kda and is derived from a larger precursor molecule. The β-amyloid precursor molecule may take on different forms, including proteins of 695, 714, 751, and 770 amino acids, since the precursor gene produces at least four principle mRNAs through alternative splicing of two exons.

PrP protein, also known as the prion protein PrP 27-30, has a molecular weight of 27 to 30 Kda and is derived from a larger protein, PrP Sc. These proteins are highly infectious and transmissible. They are present in the amyloid deposits in neurological disease such as Creutzfeldt-Jakob disease, Gerstmann Strausiler Syndrome, Scrapie, Bovine Spongiform Encephalopathy, and Kuru. These diseases are rapidly progressive neurological disorders characterized by dementia and fall into the category of subacute spongiform encephalopathies. Microscopically, the cerebral tissue is characterized by neuronal loss, gliosis, spongiform changes, and extracellular amyloid deposits in the form of plaques.

Although there exist many biochemically diverse types of amyloid deposits, the pathogenetic mechanisms that may be operating in amyloidosis in general are shared by the different types. In most cases, a circulating precursor protein may result from overproduction of either intact or aberrant molecules (plasma cell dyscrasias), reduced degradation or excretion (SAA in some secondary amyloid syndromes and β2-microglobulin in long-term hemodialysis) or genetic abnormalities associated with variant proteins (FAP). Proteolysis of a larger precursor molecule occurs in many types of amyloidosis, resulting in the production of lower MW fragments that polymerize assume a β-pleated sheet conformation and deposit as fibrils in tissues, usually in an extracellular location. Amyloid deposition is generally an irreversible pathologic process. In most instances, the constant accumulation of amyloid fibril proteins leads to progressive organ dysfunction and eventual death.

C. Animal Models for Amyloidosis

Elucidation of the pathogenesis, treatment and prevention of diseases associated with amyloid fibril deposition has been hampered by the lack of suitable in vivo experimental models that can reproduce salient features of amyloidosis. One approach that has been extensively used to study AA amyloidosis involves injecting mice with one of a variety of chemical or biological compounds including casein, silver nitrate, and lipopolysaccharide (Skinner et al., 1997; Kisilevsky et al., 1994). These agents stimulate the production of cytokines, e.g., tumor necrosis factor and interleukins 1 and 6 (IL-1 and IL-6), that mediate the inflammatory response by increasing the synthesis of serum amyloid A protein (SAA) (Sipe et al, 1994). This molecule, in turn, serves as the precursor of the polypeptide that is deposited in the spleen, liver, and kidneys of affected animals as Congophilic, green birefringent fibrils, i.e., amyloid. Amyloid deposition can be accelerated in mice injected intravenously with amyloid enhancing factor (AEF), a molecule isolated from spleens of mice with AA amyloidosis (Axelrad et al., 1982). The advantage of this model is the reproducibility of the pathologic manifestations and the predictable sites of deposition. Amyloid invariably develops within the liver, spleen, and kidney (Husebekk et al. 1985; Tape et al., 1988; Sipe et al., 1992; Husby et al., 1994). However, because cessation of the inflammatory stimulus results in disappearance of the amyloid deposits (Kisilevsky et al., 1994), the usefulness of this model is limited by the need for repeated injections and the transitory nature of the induced pathology.

Through transgenic technology, it is now possible to study the pathological effects of continuous expression of cytokines and other biological factors. Since IL-6 plays a seminal role in hematopoiesis and the inflammatory-mediated response (Kishimoto et al., 1988; Li et al., 1989; Hirano et al., 1990; Van Snick et al., 1990; Fattori et al., 1994), transgenic mice expressing the murine (mIL-6; Brandt et al., 1990; Woodroofe et al., 1992) or human (hIL-6; Suematsu et al., 1989; Fattori et al, 1989) form of this molecule have been generated. Animals carrying the hIL-6 gene under the control of either the human Eμ enhancer (Suematsu et al., 1989) or the mouse metallothionein-1 (MT-1) promoter (Fattori et al., 1989) predominantly express IL-6 in B cells or liver, respectively. The Eμ/hIL-6 transgenic mice are typified by an extensive polyclonal plasma cell proliferation within lymph nodes and spleen, as well as mesangioproliferative glomerulonephritis (Suematsu et al., 1989). The MT-1/hIL-6 animals have a sustained increase in liver-derived acute phase proteins and an IgG plasmacytosis within lymphoid tissue; in addition, these mice manifest renal pathology resembling that seen in patients with myeloma (cast) nephropathy (Fattori et al., 1989). Furthermore, systemic AA-amyloid deposition is detected in these animals when they reach 3 months of age. The extent of the amyloid deposition increases steadily with age and occurs primary in the spleen, liver, and kidneys (Solomon et al., 1999), although the heart, adrenal glands and pancreas may also be involved.

D. Methods of Treatment for Amyloidosis

Very rarely do patients with clinically proven amyloidosis spontaneously achieve complete remission, probably because the amyloid fibrils themselves are non-immunogenic. Various therapies for amyloidosis have been investigated, such as high-dose chemotherapy, steroids, iodinated doxorubicin, and stem cell replacement therapy. However, in only one type of amyloid disease, Familial-Mediterranean amyloidosis, has drug treatment (with colchicine) been shown to be effective. To date there is no treatment for Alzheimer's disease at any stage of its development. Two therapeutic reagents, Cognex and Menthane, appear to give slight relief to some victims but do not alter the course of the disease. Since Alzheimer's disease and related degenerative brain disorders are a major medical issue for an aging population, the need for new treatments and methods for diagnosing the disorders are needed. Thus, therapeutic efforts in amyloidosis have been focused on the development of compounds and agents that prevent protein aggregation leading to the formation of fibrils, as well as agents that block the initial interaction of fibrillar proteins in tissues.

A variety of studies have characterized antibodies that bind to amyloid proteins or amyloid fibrils. (See, for example, U.S. Pat. Nos. 5,714,471; 5,693,478; 5,688,651; 5,652,092; 5,593,846; 5,536,640; 5,385,915; 5,348,963; 5,270,165; 5,262,332; 5,262,303; 5,164,295; and 4,782,014.) In addition, several publications have suggested that anti-amyloid antibodies might be useful for studying the progression of beta-amyloidosis and for various therapeutic options. (See, for example, Bellotti et al., 1992; Bellotti et al., 1993; Walker et al., 1994; and Bickel et al., 1994)

U.S. Pat. No. 6,017913 teaches the use of naphthylazo compounds to inhibit amyloid aggregation in a mammal. U.S. Pat. No. 5,744,368 discloses methods and compositions for preventing aggregation of amyloid β-protein (β-AP) comprising providing a β-AP binding compound, such as transthyretin, to promote complex formation between β-AP and β-AP binding protein and prevent β-AP from self-aggregating and forming amyloid.

E. Diagnosis and Classification of Amyloid Proteins from Microscopic Slides by Analytical Procedures The diagnosis of amyloid deposition is almost exclusively done by the morphologic examination of tissue material taken from biopsy samples or autopsied organs. Positive staining with Congo red and exhibition of green birefringence in polarized light are generally accepted principles, which suggest the deposition of amyloid in the examined sample. The finding of fibrils by electron microscopy in biopsies or tissues under examination confirms the diagnosis of amyloidosis. Ongoing research in the last decades has revealed that different proteins can be deposited as amyloid fibrils. At least 18 different proteins have been discovered as constituents of amyloid so far. It is of decisive importance for the prognosis and therapy of amyloid related diseases to discover the very nature of the proteins it the deposits. Immunohistochemical methods are mostly employed to specify which protein constitutes the fibrils. But it has been frequently reported, that some antibodies used in this techniques failed to react or give only weak reactions with the proteins entwined in the amyloid fibrils though they bind specifically to the precursor molecules. Other methodical approaches have to be taken to get an unequivocal definition of the proteins, which are deposited as amyloid fibrils. Another way to reach this goal is to isolate the fibril proteins from the tissue and perform an amino acid sequence analysis of the purified protein. This procedure poses no problems in cases of systemic amyloidosis, where after an autopsy enough fresh tissue material is available for extraction. But in many cases only microscopic slides or paraffin embedded tissue blocks are available for further examination. Normally tissue samples are formalinized and dehydrated before they are embedded in paraffin. There are a few reports about sequencing formalinized material and deriving useful information about the sequence of the amyloid related protein in the sample examined.

SUMMARY OF THE INVENTION

At the present, no therapeutic agent has been demonstrated to effectively treat amyloidosis in vivo. Thus, there still exists a need for developing a method of treating amyloidoses and a method of identifying therapeutic agents that are effective in treating amyloidosis in vivo.

The present invention provides a therapeutic method for removing in vivo amyloid fibrils from a patient. The present invention also provides a transgenic animal that develops systemic AA amyloidosis within three weeks for use as a tool to investigate AA amyloidosis and to evaluate agents that may be potentially useful in preventing and treating amyloid-related disorders.

The present invention provides a transgenic non-human animal, preferably a transgenic mouse, that develops extensive AA amyloid deposits three weeks after administration of amyloid enhancing factor (AEF).

The present invention discloses a method of increasing the rate of development of amyloid deposits in a transgenic animal carrying an IL-6 gene under the control of a promoter or enhancer, comprising administering to the animal an effective amount of amyloid enhancing factor (AEF), wherein the increase in rate of development of amyloid deposits is relative to a transgenic animal not administered with AEF.

The present invention also provides a method of identifying an agent effective in preventing amyloidosis comprising administering a test agent to a transgenic animal carrying an IL-6 gene under the control of a promoter or enhancer, determining the life span of the transgenic animal, and comparing its life span to that of a control transgenic animal, wherein a longer life span of the transgenic animal administered with the test agent indicates that the test agent is effective in preventing AA amyloidosis.

The present invention teaches a method of identifying an agent effective in preventing amyloidosis comprising administering a test agent and AEF to a transgenic animal carrying an IL-6 gene under the control of a promoter or enhancer, determining the life span of the transgenic animal, and comparing its life span to that of a control transgenic animal, wherein a longer life span of the transgenic animal administered with the test agent indicates that the test agent is effective in preventing amyloidosis.

The present invention also discloses a method of identifying an agent effective in treating amyloidosis comprising administering a test agent to a transgenic animal carrying an IL-6 gene under the control of a promoter or an enhancer and having amyloid deposits in its body, determining the life span of the transgenic animal, and comparing its life span to that of a control transgenic animal, wherein a longer life span of the transgenic animal administered with the test agent indicates that the test agent is effective in treating amyloidosis.

Additionally, the present invention provides a method of identifying an agent effective in treating amyloidosis comprising administering AEF to a transgenic animal carrying an IL-6 gene under the control of a promoter or enhancer, administering a test agent, preferably three weeks later, determining the life span of the transgenic animal, and comparing its life span to that of a control newborn transgenic animal, wherein a longer life span of the transgenic animal administered with the test agent indicates that the test agent is effective in treating amyloidosis.

As an alternative embodiment, the agent effective to prevent or treat amyloidosis is identified by detecting the development of amyloid deposits by radiographic imaging, such as MRI, CT or SPECT scan, of the transgenic animal. In one aspect of the invention, a decrease or a constant level of amyloid deposits in the transgenic animal as compared to a control animal indicates that the test agent is effective in treating amyloidosis.

In a preferred embodiment, the transgenic animal is a transgenic mouse; the IL-6 gene is a human IL-6 gene; the promoter is a mouse metallothionein-I (MT-1) promoter; the enhancer is a human Eμ enhancer.

Also, the methods of the present invention can be used to identify agents effective to prevent or treat AA amyloidosis.

Moreover, the present invention provides a method of removing amyloid deposits from a patient comprising administering to the patient amyloid fibrils in an effective amount to generate an immune response that will promote the removal of in vivo amyloid fibrils from the patient. In a preferred embodiment, the amyloid fibril comprises an amyloid light chain polypeptide or whole light chain. The present invention also provides a vaccine or pharmaceutical composition comprising an amyloid fibril and a carrier. The preferred amyloid fibrils of the present invention are preformed amyloid fibrils. They may be obtained by recombinant or synthetic means.

Furthermore, the present invention provides diagnostic assays for monitoring immunoglobulin light chain fibrillogenesis in real-time. In one embodiment, the present invention discloses a method of identifying an agent that inhibits fibrillogenesis of a polypeptide comprising incubating a test agent with a polypeptide known to form fibrils and ThT, and measuring the fluorescence intensity as a function of time to determine whether the agent inhibits fibrillogenesis of the polypeptide. In another embodiment, a method of determining whether a compound is fibrillogenic comprising incubating the compound with ThT, and measuring fluorescence intensity as a function of time to determine whether the compound is fibrillogenic.

The present invention also discloses a method for identifying the chemical nature of the protein in amyloid deposits which enables the determination of the type of amyloidosis for therapeutic and prognostic purposes. The present invention includes a method of identifying the chemical nature of proteins in amyloid deposits comprising extracting the proteins from ultra-thin sections of formalin fixed, paraffin-embedded tissue biopsy specimens; isolating the proteins; and determining the amino acid sequence of each of the proteins.

BRIEF DESCRIPTION OF THE DRAWINGS

FIG. 3 compares the amino acid sequences of the first 58 residues of mouse AA amyloid versus that of protein extracted from the liver of an MT-1/hIL-6 transgenic mouse (SEQ ID NO: 1).

DETAILED DESCRIPTION OF THE INVENTION

A. General Description

Figure 1:
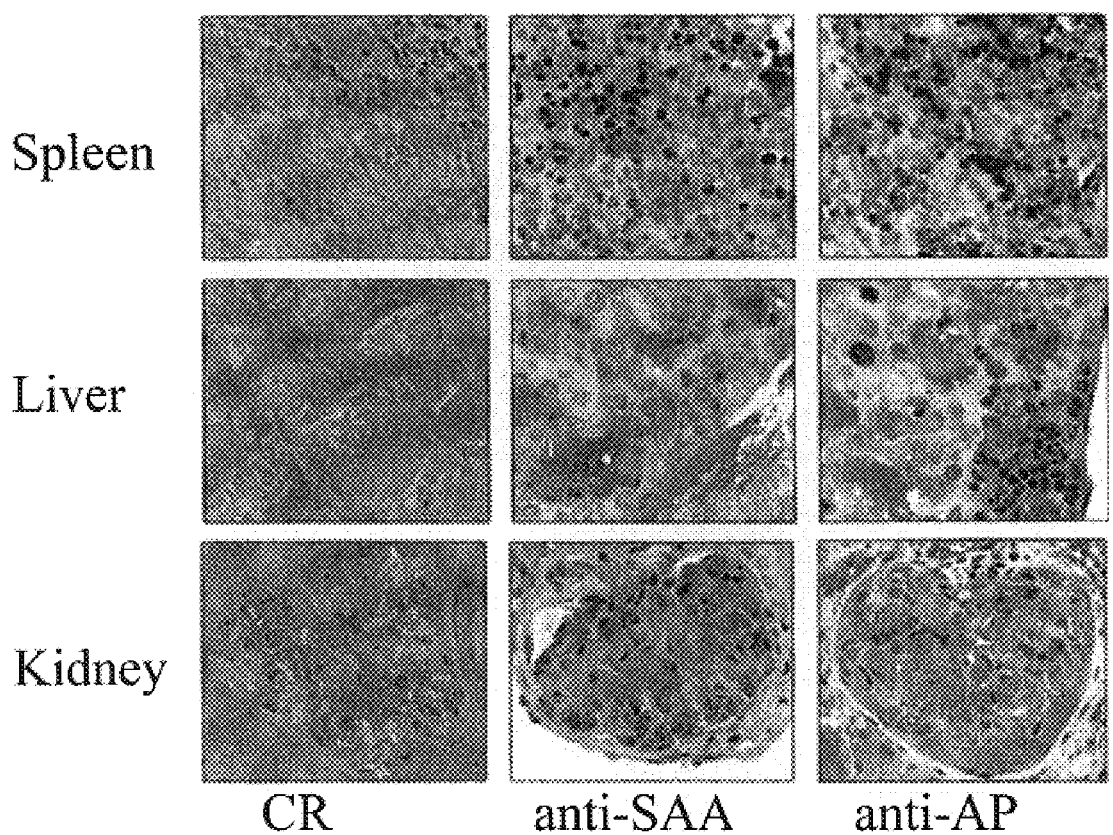
FIG. 1 shows histochemical and immunohistochemical analyses of spleen, liver, and kidney obtained from an MT-1/hIL-6 transgenic mouse. (Left panels) Polarizing microscopy of Congo red (CR) stained tissue sections (×400). (Middle and right panels) Immunoperoxidase staining with anti-SAA and anti-AP antibodies, respectively (×400).

The present invention discloses that transgenic animals carrying the human IL-6 gene under the control of a promoter, such as the metallothionein-I promoter, have markedly increased concentrations of sAA and develop amyloid in the liver, spleen, and kidneys at an early stage in life. Furthermore, these transgenic animals develop extensive amyloid deposits in the heart and pancreas in addition to the liver, spleen, and kidneys only six weeks after treatment with AEF. The present invention provides a useful transgenic animal model for investigating AA amyloidosis. The pathologic deposits in AEF-treated transgenic animals are irreversible and contribute to the death of the animal. These transgenic animals are useful not only for investigating the disease process, but also as tools for evaluating the efficacy of drugs and other agents designed to prevent and treat this disease.

The present invention also includes methods of using the transgenic animals to identify potential therapeutic agents for treating or prevent AA amyloidosis and for inhibiting the aggregation of AA amyloid fibrils. The present invention also discloses the use of the transgenic animal to investigate the disease process.

Moreover, the present invention teaches compositions, vaccines, and methods of removing amyloid fibrils from a patient comprising administering to the patient an amyloidogenic protein in fibrillar form (a synthetic amyloid fibril) that will generate an immune response effective for removal of amyloid fibrils in vivo, often in only a few days.

Further, the present invention provides diagnostic assays for monitoring immunoglobulin light chain fibrillogenesis in real-time and for identification of the chemical nature of the protein in amyloid deposits which enables the determination of the type of amyloidosis for therapeutic and prognostic purposes.

B. Specific Embodiments

1. The Transgenic Rapid, Inducible Amyloid Deposition (TRIAD) Mouse

The present invention is based in part on the discovery that transgenic mice carrying the human IL-6 gene under the control of the metallothionein-I promoter have markedly increased concentrations of sAA and developed amyloid in the liver, spleen, and kidneys by about 3 months of age (Solomon et al. 1999). At the time of death at about 9 months of age, organs obtained from these animals have extensive amyloid deposits. The AA nature of the amyloid has been evidenced immunohistochemically and has been unequivocally established by sequence analysis of protein extracted from the fibrils. This disease process is apparent radiographically using small animal computer axial tomography (CT) and magnetic resonance imaging (MRI) equipment. The availability of this unique in vivo experimental model of AA amyloidosis provides the means to assess the therapeutic efficacy of agents designed to reduce or prevent the fibrillar deposits found in AA and other types of amyloid-associated disease.

The usefulness of the transgenic mouse AA model has been extended by the discovery that the pathologic process can be induced in young, i.e., 6-week old mice, through i.v. administration of AEF. Such mice develop extensive amyloid deposits in the heart and pancreas in addition to the liver, spleen, and kidneys; these pathologic deposits, in contrast to those induced by chemical stimuli, are irreversible and lead to death of the animal.

The present invention provides a method of obtaining transgenic animals that develop AA amyloidosis after administration of AEF. As used herein the term "AEF" refers to the amyloid enhancing factor characterized by Axelrad et al. (1982). Amyloid deposition is an irreversible process and the continual infiltration by this material leads to organ failure and eventually death. The development of AA amyloidosis in the AEF-enhanced transgenic animal model provides a system not only for investigating the disease process, but also as a tool to evaluate the efficacy of drugs and other agents designed to prevent and treat this disease.

2. Transgenic Animals

The procedure for producing a transgenic animal is known in the art (B. Hogan et al., (1986); and U.S. Pat. No. 4,873,191). As used herein, a "transgenic animal" is any animal, preferably a non-human mammal, a bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation refers to the introduction of a recombinant DNA molecule. This molecule may be integrated within a chromosome, or it may be extrachromosomally replicating DNA. In the typical transgenic animals described herein, the transgene causes cells to express a recombinant form of IL-6, preferably human IL-6. The "non-human animals" of the invention include vertebrates, such as rodents, non-human primates, sheep, dog, cow, chickens, amphibians, reptiles, etc. Preferred non-human animals are selected from the rodent family including rat and mouse, most preferably mouse, though transgenic amphibians, such as members of the *Xenopus* genus, and transgenic chickens can also provide important tools for understanding, for example, embryogenesis and tissue patterning.

As used herein, the term "transgene" means a nucleic acid sequence (encoding, e.g., an IL-6 polypeptide), which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can include one or more transcriptional regulatory sequences and any other nucleic acid, such as introns, that may be necessary for optimal expression of a selected nucleic acid.

The transgene encoding a desired polypeptide, for example an IL-6 polypeptide, is linked to one or more regulatory regions. Selection of the appropriate regulatory region or regions is a routine matter, within the level of ordinary skill in the art. The regulatory regions may comprise a promoter region for functional transcription, as well as a region situated 3' of the gene of interest, and which specifies a signal for termination of transcription and a polyadenylation site. It may also include an enhancer region. Examples of enhancer include Eμ enhancer, the RSV enhancer, and SV40 enhancer. As shown in the examples, the Eμ enhancer is sufficient for expression of IL-6 in transgenic animal.

Promoters that may be used in the present invention include both constitutive promoters and regulated (inducible) promoters. The promoter may be naturally responsible for the expression of the nucleic acid. It may also be from a heterologous source. In particular, it may be promoter sequences of eukaryotic or viral genes. For example, it may be promoter sequences derived from the genome of the cell which it is desired to infect. Likewise, it may be promoter sequences derived from the genome of a virus, including the adenovirus used. In this regard, there may be mentioned, for example, the promoters of the EIA, MLP, HCMV, and RSV genes and the like. In addition, the promoter may be modified by addition of activating or regulatory sequences or sequences allowing a tissue-specific or predominant expression.

Tissue specific promoters include, for example, the keratin 5 (K5) (Missero et al., 1993) and keratin 14 (K14) (Wang et al., 1997) promoters for the basal layer of skin; keratin 1 (K1) (Johnson et al., 1985) and keratin 10 (K10) (Feng et al., 1997) promoters for the suprabasal layer of skin; loricrin (Yoneda et al., 1993), involucrin (Carroll et al., 1997; Carroll et al., 1995) and transglutaminase I (Lee et al., 1996) promoters for the granular layer of skin; cornifin β promoter (Austin et al., 1996) for squamous epithelia, and mCC10 (Ray et al., 1996) and elastin (Hsu-Wong et al., 1994) promoters for the respiratory epithelium.

Additional promoters useful for practice of this invention are the ubiquitous promoters HPRT (Rincon-Limas et al., 1994), vimentin (Vicart et al., 1994), actin (Bronson et al., 1996), and tubulin (Gloster et al., 1994); the intermediate filament promoters desmin (Lee et al., 1995), neurofilaments, keratin, and GFAP (Galou et al., 1994); the therapeutic gene promoters MDR (Yang et al., 1996), CFTR (Matthews et al., 1996), and factor VIII (McGlynn et al., 1996); promoters which are preferentially activated in dividing cells; promoters which respond to a stimulus such as steroid hormone receptor (Cicatiello et al., 1995) and retinoic acid receptor (Mendelsohn et al., 1994) promoters; tetracycline-regulated transcriptional modulators (Furth et al., 1994); cytomegalovirus immediate-early; retroviral LTR (Choate et al., 1996), metallothionein-1 (Fattori et al., 1994); SV-40; E1a and MLP promoters. Tetracycline-regulated transcriptional modulators and CMV promoters are described in WO 96/01313, U.S. Pat. Nos. 5,168,062 and 5,385,839, the contents of which are incorporated herein by reference.

Generally, a method for producing a transgenic animal, which can be stably bred to produce offspring containing the gene, comprises the following steps:
  (a) isolating a fertilized oocyte from a first female animal;
  (b) transferring the transgene into the fertilized oocyte;
  (c) transferring the fertilized oocyte containing the transgene to the uterus of the same species as the first animal;
  (d) maintaining the second female animal such that
    (i) the second female animal becomes pregnant with the embryo derived from the fertilized oocyte containing the transgene,
    (ii) the embryo develops into the transgenic animal, and
    (iii) the transgenic animal is viably born from the second female animal;

wherein the transgenic animal has the genetic sequence for the desired protein and is capable of being bred to produce offsprings having cells stably containing the desired genetic sequence.

3. Method of Using the TRIAD Mouse for Identifying Potential Agents for Prevention or Treatment of Amyloidosis As set forth above, the present invention includes a method for identifying potential therapeutic agents for preventing and treating inflammation-associated, AA amyloidosis. The present invention also includes a method for identifying agents that inhibit the aggregation of AA amyloid fibrils.

In one assay format, a test agent is administered to transgenic animals, preferably six weeks old, carrying an IL-6 gene, preferably the human IL-6, under the control of a promoter, preferably the metallothionein-1 promoter, or an enhancer, the Eµ enhancer. For control, transgenic animals carrying an IL-6 gene under the control of a promoter or enhancer and receiving no test agent or receiving a control agent similar in nature to the test agent are raised under the same environmental conditions as the transgenic animals administered with the test agent. The life span of the transgenic animals is ascertained and compared. A longer life span for transgenic animals administered with a test agent as compared to the control transgenic animals indicates that the test agent is an effective therapeutic agent in preventing AA amyloidosis.

In another assay format, a test agent and AEF is administered to transgenic animals, preferably six weeks old, carrying an IL-6 gene, preferably the human IL-6 gene, under the control of a promoter, preferably the metallothionein-1 promoter, and/or an enhancer, preferably the Eµ enhancer. Similar to the assay above, control transgenic animals are administered with only AEF or AEF and a control agent similar in nature to the test agent and are raised under identical environmental conditions as transgenic animals administered with both the test agent and AEF. The life span of the transgenic animals is ascertained and compared. A longer life span for transgenic animals administered with a test agent as compared to control transgenic animals indicates that the test agent is an effective therapeutic agent in preventing AA amyloidosis.

In a third assay format, a test agent is administered to transgenic animals carrying an IL-6 gene, preferably the human IL-6 gene, under the control of a promoter, preferably the metallothionein-1 promoter, and/or an enhancer, preferably the Eµ enhancer, and having amyloid deposits in its body. For control, transgenic animals carrying an IL-6 gene under the control of a promoter or enhancer and receiving no test agent or receiving a control agent similar in nature to the test agent are raised under the same environmental conditions as the transgenic animals administered with the test agent. The life span of the transgenic animals is ascertained and compared. A longer life span for transgenic animals administered with a test agent as compared to the control transgenic animals indicates that the test agent is an effective therapeutic agent in treating AA amyloidosis.

In a fourth assay format, AEF is administered to transgenic animals carrying an IL-6 gene, preferably the human IL-6 gene, under the control of a promoter, preferably the metallothionein-1 promoter, and/or an enhancer, preferably the Eµ enhancer. After AEF injection, for instance at three weeks, a test agent is administered to the transgenic animal injected with AEF. Similar to the assay above, control transgenic animals, administered with only AEF or AEF and a control agent similar in nature to the test agent, are raised under identical environmental conditions as transgenic animals administered with both AEF and the test agent. The life span of the transgenic animals is ascertained and compared. A longer life span for transgenic animals administered with AEF and a test agent as compared to control transgenic animals indicates that the test agent is an effective therapeutic agent in treating AA amyloidosis.

To determine whether a test agent inhibits amyloid formation, the four assays described above may be modified. Instead of ascertaining the life span of the transgenic animals, the animals are sacrificed, for instance at eight weeks after AEF administration or eight months if AEF is not administered. Histochemical and/or immunohistochemical analyses of organs from the animals, such as the spleen, liver, kidney, heart, and pancreas, are performed to confirm the presence, absence, or extent of amyloid deposits. Alternatively, radiographic imaging via MRI, CT, or SPECT scan on small transgenic animals may be performed to detect amyloid deposits without sacrificing the animal, and the life span of the transgenic animal can still be determined.

Agents that are capable of preventing, delaying the onset, or retarding the development of AA amyloidosis are potentially effective in preventing the aggregation of AA into amyloid fibrils. Agents that are-capable of removing established AA amyloid deposits and/or decreasing the extent of amyloid deposition within the organs are potentially effective as mediators in the removal of amyloid fibrils.

As used herein, the term "a test agent" refers to any agent that is to be tested. A test agent can be, but is not limited to, a chemical compound, a peptide, a polypeptide, a carbohydrate, or an antibody. A skilled artisan can readily recognize that there is no limit as to the structural nature of the test agents of the present invention.

A test agent that is assayed by the above method can be randomly selected or rationally selected or designed. As used herein, an agent is said to be randomly selected when the agent is chosen randomly without considering the specific structures or mechanisms involved in the development, treatment, or prevention of AA amyloidosis or inhibition of amyloid fibrillogenesis (i.e. the aggregation of amyloidogenic proteins into fibrils). An agent is said to be rationally selected or designed when the agent is chosen on a nonrandom basis which takes into account the structures, i.e. compares the structures to those of known agents that are effective in treating and preventing AA amyloidosis or inhibiting amyloid aggregation. For example, a rationally selected peptide could be a molecule that binds AA amyloid fibrils and prevents the growth of those fibrils by blocking the addition of protein to the amyloid fibril.

4. Administration of Test Agent to Transgenic Animal

The test agents of the present invention can be administered to the transgenic animal via parenteral, subcutaneous, intravenous, intramuscular, intraperitoneal, transdermal, or buccal routes. Alternatively, or concurrently, administration may be by the oral route. The dosage administered will be dependent upon the age and weight of the transgenic animal, frequency of treatment, the nature of the effect desired, as well as the toxicity of the agent and the pharmacokinetics of the agent in the animal. For example, as a means of inhibiting amyloid fibril formation by preventing the aggregation of protein, removing established amyloid deposits, or preventing amyloidosis by other means, the test agent is administered systemically or locally to the transgenic animal being treated. As described below, there are many methods that can readily be adapted to administer such agents.

While individual transgenic animal may vary, a determination of optimal ranges of effective amounts of each component in the composition is within the skill of the art. Typical dosages comprise 0.1 to 100 mg/kg body wt. The preferred dosages comprise 0.1 to 10 mg/kg body wt. The most preferred dosages comprise 0.1 to 1 mg/kg body wt.

In addition to the pharmacologically active agent, the compositions of the present invention may contain suitable pharmaceutically acceptable carriers comprising excipients and auxiliaries which facilitate processing of the active compounds into preparations which can be used pharmaceutically for delivery to the site of action. Suitable formulations for parenteral administration include aqueous solutions of the active compounds in water-soluble form, for example, water-soluble salts. In addition, suspensions of the active compounds as appropriate oily injection suspensions may be administered. Suitable lipophilic solvents or vehicles include dimethyl sulfoxide, or fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran. Optionally, the suspension may also contain stabilizers. Liposomes can also be used to encapsulate the agent for delivery into the cell.

The pharmaceutical formulation for systemic administration according to the invention may be formulated for enteral, parenteral, or topical administration. Indeed, all three types of formulations may be used simultaneously to achieve systemic administration of the active ingredient.

Suitable formulations for oral administration include pulverized preparations mixed with food, hard or soft gelatin capsules, pills, tablets, including coated tablets, elixirs, suspensions, syrups, or inhalations and controlled release forms thereof.

5. Synthetic Amyloid Fibrils for Removing In Vivo Amyloid Fibrils

The present invention is based in part on the finding that the use of anti-amyloid antibodies together with the body's cellular immune defense system can effect the removal of the pathologic amyloid deposits. Immunizing mice with synthetic AL amyloid fibrils formed in vitro from a recombinantly derived immunoglobulin light chain variable-region protein generates in vivo anti-fibril antibodies reactive with AL, as well as other types of amyloid (e.g., AA, A, etc). The mice may also be immunized with the complete light chain protein, i.e. the variable and the constant region together. The immunogen may be composed of any protein, peptide, polyamino acid, or other synthetic polymer which is capable of forming amyloid-like fibrils defined by having the correct ultrastructural and biochemical properties. When such mice are injected subsequently with human AL extracts, this material is removed within 5 days as compared to more than 30 days in non-immunized animals. The use of this particular synthetic AL amyloid fibril and related AL amyloid fibrils as a vaccine is of potential clinical benefit in the treatment and prevention of primary (AL) amyloidosis as well as other types of amyloid-associated disorders, e.g., adult onset (type 2) diabetes and Alzheimer's Disease.

As used herein, the term "homologous amyloid fibrils" refers to synthetic fibrils used as the immunogen in the vaccine that are of the same type as those found in the amyloid in the patient, e.g., light chain fibrils used to treat a patient with AL amyloidosis or synthetic AA-fibrils used to treat AA-amyloid. In contrast, as used herein, the term "heterologous amyloid fibrils" refers to synthetic fibrils used in the vaccine that are different from the amyloid in the patient, i.e. light chain fibrils used to treat AA-amyloidosis.

The present invention provides a method of removing in vivo amyloid fibrils from a patient comprising administering to the patient an effective amount of synthetic amyloid fibril or related amyloid fibril, structurally comparable (or similar) to the fibril found in the amyloid deposit of the patient. There is evidence that both homologous and heterologous amyloid deposits in the mice can be cleared by immunization with synthetic light chain fibrils.

As used herein, the term "an effective amount of amyloid fibril" refers to an amount of amyloid fibrils that for example, may be effective to perform an activity, such as to increase removal of endogenous or in vivo amyloid fibrils by about 10%, 20%, 30%, 40%, or preferably 50% or more compared to the untreated condition. In the most preferred embodiment, the effective amount increases the efficacy of removal so that essentially all of the amyloid fibrils are removed.

Other isolated proteins identified in amyloid deposits including immunoglobulin light chains, serum amyloid A protein, β2-microglobulin, transthyretin, cystatin C variant, gelsolin, procalcitonin, PrP protein, ApoAI, β-amyloid protein (β/A4), and lysozyme can also be used to immunize patients with amyloidosis and to remove in vivo amyloid fibrils from the patients body and to prevent subsequent accumulation of amyloid deposits.

As used herein, the term "amyloid fibril" refers to protein aggregates which possess the ultrastructural, biochemical, physical, or tinctorial properties of amyloid fibrils formed in vivo. As used herein, the term "amyloid protein" refers to proteins or peptides that are capable of forming amyloid fibrils, to the protein present in the amyloid deposit of a patient, to allelic variants thereof, variants thereof, and to peptides thereof. Allelic variants, though possessing a slightly different amino acid sequence than a naturally occurring amyloid polypeptides, will still have the requisite ability to aggregate and form amyloid fibrils. The term also includes variants of amyloid proteins having amino acid alterations that do not adversely affect the ability of the amyloid fibril to aggregate. A substitution, insertion, or deletion is said to adversely affect the amyloid protein when the altered sequence prevents it from aggregating into fibrils. For example, the overall charge, structure or hydrophobic/hydrophilic properties of amyloid protein can be altered without adversely affecting the activity of the amyloid protein. Accordingly, the amino acid sequence of amyloid protein can be altered, for example, to render the protein more hydrophobic or hydrophilic, without adversely affecting the activity of the protein. The term, "amyloid fibril", encompasses, but is not limited to, fibrils composed of immunoglobulin light chains, serum amyloid A protein, β2-microglobulin, transthyretin, cystatin C variant, gelsolin, procalcitonin, PrP protein, amyloid β-protein, peptides thereof, variants thereof, and allelic variants thereof.

As used herein, the term "synthetic amyloid fibril" or "synthetic amyloid protein" refers to an amyloid fibril or constituent protein obtained by synthetic means. The term encompasses amyloid fibril-forming-proteins and polypeptides having the same amino acid sequence as the proteins or polypeptides present in amyloid deposits, allelic variants thereof, variants thereof, and peptides thereof obtained by synthetic means.

As used herein, the term "recombinant amyloid protein" refers to a protein or peptide capable of forming amyloid fibrils that is obtained by recombinant means. The term encompasses but is not limited to, proteins and polypeptides having the same amino acid sequence as the polypeptides present in the amyloid deposit, allelic variants thereof, variants thereof, and peptides thereof obtained by synthetic means.

The present invention can be practiced with amyloid fibrils composed of naturally occurring amyloid protein obtained by synthetic or recombinant means, or isolated from its native source. The present invention can also be practiced with amyloid fibrils composed of a peptide of an amyloid protein, an allelic variant of an amyloid protein, or a variant of an amyloid protein, provided that the peptide or variant when in fibrillar form generates an immune response that promotes the removal of amyloid fibrils from the patient.

6. Pharmaceutical Compositions that Generate an Immune Response for Removal of Amyloids Fibrils The pharmaceutical compositions for therapeutic treatment according to the present invention are intended for any form of administration including, parenteral, oral, or local administration. Preferably, the pharmaceutical compositions are administered orally or parenterally, e.g., intravenously, subcutaneously, intradermally, or intramuscularly. Delivery of amyloid fibrils across the blood-brain barrier (BBB) may be achieved through liposomal or micellar delivery. Alternatively, the amyloid fibrils of this invention can be delivered directly into the cerebrospinal fluid (Walker et al., 1994). For other delivery mechanisms, refer to P. M. Friden, 1996 U.S. Pat. No. 5,527,527 and W. M. Pardridge, 1991 U.S. Pat. No. 5,004,697. All of the above documents are incorporated herein by reference.

Thus, the invention provides compositions and vaccines for parenteral administration which comprise a solution of amyloid fibril dissolved or suspended in a pharmaceutically acceptable carrier, preferably an aqueous carrier. A variety of aqueous carriers may be used, e.g., water, buffered water, 0.4% saline, 0.3% glycine, hyaluronic acid and the like. These compositions may be sterilized by conventional, well known sterilization techniques, or may be sterile filtered. The resulting aqueous solutions may be packaged for use as is, or lyophilized,'the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The concentration of amyloid fibrils of the invention in the pharmaceutical formulations can vary widely, i.e., from less than about 1%, usually at or at least about 10-15% to as much as 50% or more by weight, and will be selected primarily by fluid volumes, viscosities, etc., in accordance with the particular mode of administration selected.

Without undue experimentation, one of ordinary skill in the art could determine the quantity of amyloid fibril that would be effective to adequately generate an immune response for removal of the in vivo amyloid fibrils. Amounts effective for this use will depend on, e.g., the nature of the amyloid protein composition, the manner of administration, the stage and severity of the disease being treated, the weight and general state of health of the patient, the toxicity of the preparation, the pharmacokinetics of catabolism and clearance, and the judgment of the prescribing physician. A typical single dose of 5 mg/kg per injection could generally be used. It must be kept in mind that the amyloid protein and peptide compositions derived therefrom may be employed in serious disease states, that is, life-threatening or potentially life-threatening situations. In such cases it is possible and may be felt desirable by the treating physician to administer substantial excesses of these compositions.

As noted earlier, any amyloid fibril that generates an immune response sufficient to remove amyloid fibrils from the patient may be administered to the patient. Amyloid fibrils may also be conjugated to a carrier, such as bovine serum albumin (BSA), keyhole limpet hemocyanin (KLH) or thyroglobulin, to increase their immunogenicity. Various adjuvants may also be used to increase immunological response. Such adjuvants include, but are not limited to, Freund's, mineral gels such as aluminum hydroxide, and surface active substances such as lysolecithin, pluronic polyols, polyanions, peptides, oil emulsions, and dinitrophenol. Among adjuvants used in humans, BCG (bacilli Calmette-Guerin), Corynebacterium parvum, and aluminum hydroxide (ALUM) are especially preferable.

The particular manner in which an amyloid fibril of this invention can be bonded to a carrier-protein will depend on the functionalities which are available on the peptide and the carrier, the number of peptide groups to be conjugated, etc. Groups which find use include amino groups; or carboxyl groups which can be activated by employing the mixed carbonic acid anhydride or carbodiimide; imidates; diazo groups; alpha-haloketones; and the like. Peptides or peptide-protein conjugates can be injected in the fluid state; adsorbed to insoluble particles, such as alumina; or incorporated in matrix materials such as agar, calcium alginate, or Freund's adjuvants ("complete" or "incomplete"). Other adjuvants include polyacrylamide gel, bentonite, and proteins such as methylated bovine serum albumin. Complete Freund's adjuvant, a suspension of mycobacteria in oil, is given with an aqueous preparation of the immunogen in the form of an emulsion stabilized with lanolin, lanolin derivatives, e.g., Aquaphor, mannide mono-oleate or Arlacel A. The complete adjuvant is distinguished from the incomplete adjuvant, by having mycobacteria, e.g., M. butyricum or M. tuberculosis.

The fibril conjugates can be injected interperitoneally, intramuscularly, subcutaneously, etc. When employing Freund's adjuvants, usually in combination with saline, the amount of immunogen employed will vary depending on the particular immunogenic material and the number and period of prior injections. Usually, about 0.1 to 5 mg of immunogenic material will be employed per ml of solution. The total amount of immunogenic material and solution will depend on the size, nature, and weight of the subject. The initial injection will normally be at a number of sites, aliquots of the composition being employed.

Treatment of humans with amyloidosis according to the present invention could also be applied to animals susceptible to amyloidosis, such as cows, sheep, goats, dogs, cats, or chickens. Thus, references to human patients and transgenic mice herein apply also to non-human patients.

7. Chemical Identification of Amyloid using Ultra-Thin Sections of Formalin-Fixed, Paraffin-Embedded Tissue Sections In many cases, only microscopic slides or paraffin embedded tissue blocks are available for further examination of amyloid fibrils found in a patient. Normally, tissues samples are formalinized and dehydrated before they are embedded in paraffin. The present invention discloses a method that uses ultra-thin sections of formalin fixed, paraffin-embedded tissue biopsy specimens for precise identification of the nature of the tissue deposits. The extraction, purification, and digestion procedures has been miniaturized in order to obtain usable information about the amino acid sequence of amyloid fibril forming proteins from microscopic slides or paraffin embedded tissue. The present invention provides a method to rapidly determine the type of protein deposited as amyloid.

8. In vitro Microplate Assay to monitor Immunoglobulin Light Chain Fibrillogenesis in Real-Time The present invention is also based in part on a microplate based method to quantitate the rate and extent of fibril formation. Samples are placed in a 48- or 96 well microplate containing the amyloidophilic fluorescent dye thioflavin T (ThT). The fluorescence intensity of ThT at a specific wavelength is proportional to the fibril content of the solution. The fluorescence intensity is measured.

This assay is rapid and reproducible and is useful for investigating the basic principles governing light chain fibrillogenesis. This assay can also be used to study other types of amyloid-associated proteins, such as β/A4, TTR, etc., or to investigate whether a compound is fibrillogenic.

This assay also provides a method of screening for therapeutic inhibitors of light chain fibril formation in a rapid, reproducible fashion. A test agent is incubated with a polypeptide, preferably immunoglobulin light chain, known to form fibrils and ThT. The fluorescence intensity is measured as a function of time. As a control, the fluorescence intensity of a sample containing only the polypeptide and ThT is measured as a function of time. The test agent is an inhibitor, if the fluorescence intensity does not increase with time. A variety of test agents can be screened at the same time using microplates containing a fibrillogenic polypeptide and ThT.

In light of the foregoing general discussion, the specific examples presented below are illustrative only and are not intended to limit the scope of the invention. Other generic and specific configurations will be apparent to those persons skilled in the art.

EXAMPLES

A. Transgenic Mouse Exhibiting AA Amyloidosis

1. Materials and Methods

Generation of Transgenic Animals

Transgenic mice carrying the hIL-6 cDNA under the control of the mouse MT-I promoter and Eμ enhancer were generated as described by Fattori et al (1994). Briefly, a gel-purified 4.25 Kb PvuII-PvuII DNA fragment containing the hIL-6 cDNA was cloned downstream of the MT-I promoter and microinjected into the pronuclei of fertilized eggs of a cross F1 (C57BL/6JXDBAII) mouse.

Southern Blot Analysis

Tail-derived DNA was isolated and digested with PvuII (New England Biolabs, Beverly, Mass.). Southern blots were performed (Sim et al., 1979) using a purified, labeled IL-6-specific DNA fragment as a probe. The blots were hybridized and washed under stringent conditions (65° C., 0.1×SSC) and exposed to x-ray film overnight.

Polymerase Chain Reaction (PCR)

Mice were genotyped for the presence of the transgene through analyses of the genomic DNA. IL-6 specific primers were designed for amplifying a 450-bp fragment containing the internal segment of the hIL-6 gene. The sequence of the upstream primer (IL-6For) was 5' ACC TCT TCA GAA CGA ATT GAC AAA 3' while that of the downstream primer (IL-6Rev) was 5' AGC TGC GCA GAA TGA GAT GAG TTG T 3'. One μg of genomic mouse DNA isolated from tail clippings served as the template for 30 cycles of PCR amplification using a commercial kit (Applied Biosystems-Perkin Elmer, Foster City, Calif.) and 0.5 μM of each primer (final concentration) in a total reaction volume of 100 μl. The time and temperature for each cycle were: denaturation—1 minute, 94° C.; annealing—1 minute, 60° C.; and extension—1.5 minutes, 72° C. (for the first and last cycle, the reaction times were extended to 3 and 7 minutes, respectively).

Histopathology

For light microscopy, 4 to 6 μm tissue sections were cut and stained with hematoxylin-eosin. To detect amyloid, the sections were also treated with a freshly prepared alkaline Congo red solution and viewed under polarized light using a Leitz filter polarizer with a gypsum plate and a filter analyzer. For electron microscopy, Epon®-embedded sections were examined with a Zeiss 9S transmission electron microscope and photographed.

Immunohistochemistry

Six μm paraffin-embedded tissue sections were cut on a microtome, mounted on poly-L-lysine-coated slides, dried overnight at room temperature, and deparaffinized. Immunostaining was performed using the avidin biotin complex (ABC) technique (Vector Laboratories, Burlingame, Calif.) as described previously (Solomon et al, 1990). The primary antibodies included: 1) rabbit anti-mouse SAA; 2) an affinity-purified goat anti-mouse IgG (H+L) horseradish peroxidase conjugate (Bio-Rad Laboratories, Richmond, Calif.); and 3) sheep anti-mouse serum AP (SAP). A biotinylated sheep anti-rabbit globulin antiserum was used as the secondary antibody.

Protein Assays

Serum concentrations of mouse SAA were measured by ELISA according to directions supplied by the manufacturer (Biosource, Camarillo, Calif.). Briefly, sera were collected from transgenic and control mice and analyzed using a commercial cytoscreen immunoassay kit and a specific rat anti-human SAA MoAb. A standard curve was made from known amounts of mouse SAA protein and absorbance was measured at 405 nm with a model 450 Bio Rad plate reader (Bio Rad, Richmond, Calif.). Serum IL-6 activity was assayed using the 7TD1 proliferation assay (Van Snick et al., 1990) and hIL-6 recombinant protein (GIBCO-BRL, Bethesda, Md.). A standard curve was prepared from 1, 10, 100, and 1000 pg/ml of hIL-6 in a final sample volume of 100 μl. One unit of IL-6 corresponded to 1 and 7 pg of mouse and human IL-6, respectively.

Amyloid Extraction and Purification

The methods employed for extraction of amyloid from tissue were as described by Pras et al. (1968). Mouse tissue was homogenized with cold saline in an ice bath using an Omni-Mixer (Omni International, Inc., Waterbury, Conn.). The extract was centrifuged at 10,000 rpm for 30 minutes at 4° C. and the pellet re-extracted twice more with cold saline, once with 0.1 M sodium citrate Tris-buffered saline, pH 8.0, and then again with saline until the A280 (absorbance at 280 nm) of the supernatant was <0.10. The resultant 10,000-rpm pellet was homogenized with cold distilled water, and the extract centrifuged at 35,000 rpm for 3 hours at 4° C. The pellet obtained from the water extract was then lyophilized.

One mg of extracted amyloid protein was dissolved in a 6M guanidine-HCl/0.25 M Tris-HCl, pH 8 buffer, reduced and alkylated (Eulitz et al., 1996) and purified using an ABI Model 151 HPLC apparatus and a Brownlee Aquapore 300A C8 reversed-phase 210×4.6 mm column (Perkin-Elmer, Norwalk, Conn.) with a 0.1% TFA/70% acetonitrile/water (v/v) linear gradient at a flow rate of 1 ml/minute (Eulitz et al., 1996). Protein was detected by absorbance at 220 nm, and fractions were collected manually.

Sequence Analysis

Automated sequence analyses by Edman degradation were performed using an ABI model 477A pulsed liquid sequenator; the resulting phenylthiohydantoin (PTH) amino acids were identified with an on-line ABI model 120A PTH amino acid analyzer.

Mass Spectroscopy

Mass spectroscopy was performed at the University of Tennessee Mass Spectroscopy Center that houses an electrospray ionization triple quadrapole instrument (Quattro II, Micromass, Manchester, England). The multiple charged peaks were resolved to their true molecular mass (Mr) by the MaxEnt program contained within the Max Lynx software package, as supplied by the manufacturer.

Magnetic Resonance Imaging (MRI)

Multiple spin echo images were obtained on a Bruker AMX-400 NMR spectrometer (9.3 Telsa, 89 mm bore). A Bruker imaging probe with a 25 mm coil was used with repetition time of 2 seconds, an echo time of 8.3 milliseconds, and a 2.0 mm slice thickness. Images represent the average of two acquisitions.

Computer Axial Tomography (CT)

High resolution x-ray computed tomography images were acquired using the Oak Ridge National Laboratory Micro-CAT apparatus designed specifically for small laboratory animals. The MicroCAT uses a 1024×1024 element CCD-based detector with an intrinsic spatial resolution of ~50 mm and a data acquisition rate of ~30 projections per minute. Typical data sets consist of 180 projections for screening studies and 500 for high-resolution studies. Two- and three-dimensional reconstructed images were obtained using a cone-beam filtered back-projection algorithm.

2. Results

Molecular Characterization of Transgenic Mice

Two MT-I/hIL-6 transgenic female mice (designated #3 and #4) and a wild-type male (# 5), generated as described by Fattori et al. (1994), were used to establish a breeding colony at the University of Tennessee Medical Center. The presence of the hIL-6 gene in the female carriers was verified by Southern blot analysis and PCR amplification of DNA obtained from tail clippings using a probe and primers specific for IL-6. The first mating of mice #3 and #5 yielded five offsprings, two of which carried the hIL-6 transgene as evidenced by the presence in Southern blots of the characteristic 4.25 kb PvuII band (Fattori et al., 1994).

Clinical and Laboratory Feature

The two hIL-6 transgenic mice appeared healthy until ~8 to 9 months of age when they assumed a hunched appearance and became increasingly moribund. Their serum IL-6 and SAA concentrations were markedly elevated (46 units/ml and 1067 µg/ml, respectively), as compared to an age-matched wild-type (control) mouse in which these components were virtually undetectable. Additionally, the transgenic animals had a profound polyclonal hypergammaglobulinemia and renal failure as evidenced by proteinuria and an increased blood urea nitrogen of 79 mg per dl. X-ray studies revealed hepatosplenomegaly and osteopenia.

Pathologic Feature

The salient pathology found in mouse #4 (euthanized at eight months of age) was confined to the spleen, liver, kidney, and bones. The spleen was greatly enlarged and measured 42 mm in length by 10 mm in width. The cut surface had a white, mottled appearance, and by light microscopy, a pronounced plasma cell infiltrate and extramedullary hematopoiesis were seen. The liver was also enlarged, and its visceral surface was covered by an exaggerated reticular pattern; portal areas appeared as red, triangular foci in the pale surface. The adjacent hepatocytes were atrophic and the lumens of the sinusoids were narrowed. A prominent perivenular granulocytic infiltration was noted. The kidneys, while normal in size, were pale in appearance. Histologically, the renal glomeruli were atrophic, and the tubules dilated and filled with proteinaceous casts.

A thick perivascular cuff of plasmacytoid cells surrounded renal blood vessel walls. The bones were fragile with marked osteopenia characterized by thin cortices and loss of cancellous bone. Granulocytic and megakaryocytic hyperplasia and scattered foci of plasmacytoid cells were present in the bone marrow and lymph nodes. Congo red-staining of tissues (FIG. 1) revealed that, under polarizing microscopy, the mottled areas in the spleen contained green birefringent perifollicular deposits. The spaces of Disse within the liver were widely distended by a Congophilic hyaline substance that exhibited spotty green birefringence and occupied ~50 to 80 percent of the section. Additionally, green birefringent Congophilic deposits were noted in most glomeruli and throughout the renal medulla. In contrast, the tubular casts were Congo red-negative. Sections of the spleen, liver, and kidney treated with sulfated alcian blue revealed that the Congophilic areas were also stained by the this reagent.

Electron Microscopy

Figure 2:
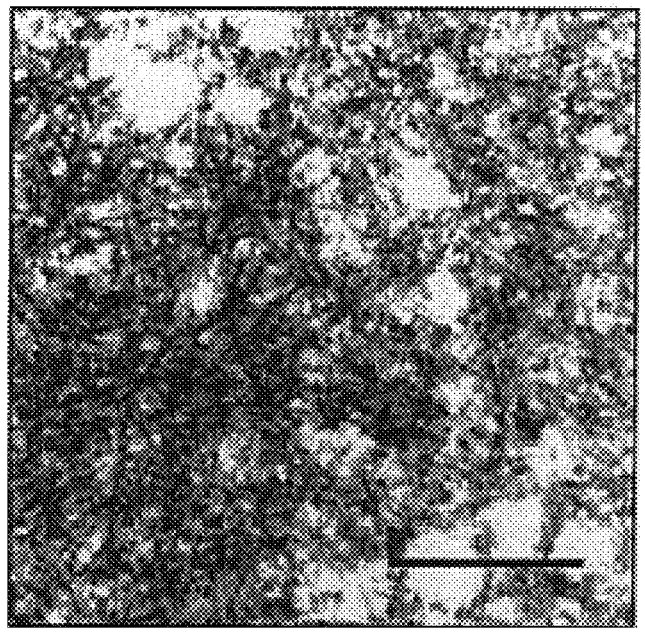
FIG. 2 shows electronphotomicrographs of fibrils extracted from the liver and kidney of an MT-1/hIL-6 transgenic mouse (×60,000; bar=325 nm).
Figure 2:
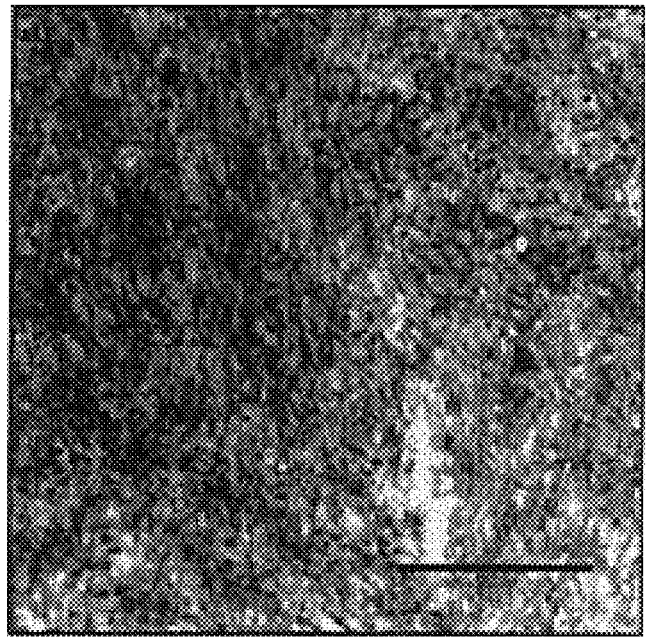

Areas corresponding to Congophilic, green birefringent material seen in the hepatic parenchyma were found by electron microscopy to contain unbranched fibrils 6 to 10 nm in diameter (FIG. 2). Similar material was also present in the spleen and kidneys.

Immunohistochemistry

Serial sections of spleen, liver, and kidney from mouse #4 were examined using a polyclonal anti-mouse SAA antiserum. Immunohistochemical analyses revealed that the Congophilic material present in the splenic and hepatic parenchyma and renal glomeruli represented AA protein. When tested against an antibody specific for the mouse amyloid-associated P component, AP, this molecule was also detected in the pathologic deposits (FIG. 1). Additionally, AA protein was found in the non-Congophilic renal tubular casts as was mouse IgG and AP.

Chemical Analyses

Approximately 60 mg of water-soluble protein was extracted from 217 mg (dry weight) of hepatic tissue and purified by HPLC. The protein contained in the major HPLC peak consisted of a single species as evidenced by SDS/PAGE. Direct (automated) analysis of this component yielded 58 amino acid residues that were identical in sequence to the amino-terminal portion of the murine $SAA_2$ protein (the amyloid forming protein; FIG. 3). Similar results were obtained when amyloid protein extracted from the spleen was purified by HPLC and sequenced; additionally, ~50 percent of this material consisted of murine histone H2b-F. By mass spectroscopy, the predominant Mr of the purified hepatic amyloid was 8,636.4 daltons, a value virtually identical to that calculated from the amino acid composition of the first 77 amino acid residues of mouse $SAA_2$ (Meek et al., 1986). Trace amounts of molecules having Mrs of 8,434.1, 8,565.3, and 8,751.4 daltons also were detected which corresponded to the first 75, 76, and 78 residues, respectively, of this protein.

Radiographic Imaging

Figure 4:
FIG. 4 shows radiographic imaging of MT-1/hIL-6 transgenic mice. (Left) MRI scan, T-1 weighted image, 10-month-old mouse. (Right) CT scan, negative contrast, 8-month-old mouse.
Figure 4:
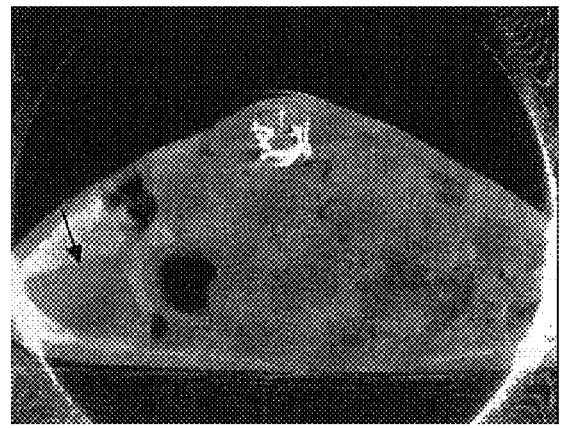

The enlarged spleen noted in the MT-I/hIL-6 mouse was especially evident in MRI and CT scans using equipment designed for small animal imaging (FIG. 4). In particular, the mottled areas that contained the amyloid deposits were visualized by MRI. In control, age-matched mice, the spleen was not visible by these techniques (not illustrated).

3. Discussion

Transgenic mice expressing hIL-6 under control of the mouse MT-I promoter developed within the spleen, liver, and kidneys extensive pathologic deposits that had the characteristic tinctorial and ultrastructural features of amyloid; namely, they were Congophilic and exhibited green birefridgence when examined under polarized light and, by electron microscopy, were fibrillar in nature. Immunohistochemical studies revealed that this material reacted with a specific anti-mouse SAA antiserum. Amino acid sequence analysis of HPLC-purified fibrillar protein extracted from the liver and spleen confirmed the murine AA nature of the amyloid and that it was derived from the amyloidogenic $SAA_2$ isoform (Meek et a., 1986). The Mr of the predominant component extracted was ~8,600 daltons and was comparable to that of human and other experimental forms of AA amyloidosis (Kisilevsky et al., 1994). The presence of other molecules associated with amyloid deposition, e.g. AP component and highly sulfated glycosoaminoglycans (Sipe et al., 1994) was also evidenced. Additionally, histones, that have been found in association with AA amyloid (Foyn et al., 1994; Prelli et al., 1991; Nordstoga et al., 1994) were detected in splenic extracts. Thus, the anatomic location and molecular features of the amyloid deposits found in the MT-I/hIL6 transgenic mice were identical to that typically occurring in experimental models in which AA amyloidosis is induced by inflammatory stimuli (Skinner et al., 1997; Kisilevsky et al., 1994; Sipe et al., 1994).

Amyloid deposition in the MT-I/hIL-6 transgenic mice was age-dependent. The pathologic deposits were first evident at three months of age and increased over the next six months with the animals becoming obviously ill. The progressive nature of the deposition, particularly within the spleen, was readily ascertained by serial MRI examinations using small animal, high-resolution radiographic techniques. Notably, this technology (as well as that utilizing radiolabeled P component (Gillmore et aL, 1997)) will make it possible to monitor non-invasively the effects of therapeutic agents designed to prevent or reverse amyloid formation.

4. Conclusion

The MT-I/hIL-6 transgenic mouse provides a unique in vivo system in which to study the pathogenesis of AA amyloid. The spontaneous development of amyloidosis in such animals is not dependent upon injection of chemical or biologic agents. Further, disease progression, as evidenced by the mottled splenic and hepatic deposits in the enlarged organs, can be readily visualized using non-invasive imaging technology. Thus, these genetically engineered animals are especially valuable in investigations of the therapeutic efficacy of compounds designed to inhibit fibril formation or effect resolution of amyloid deposits.

B. TRIAD Mouse

The "Transgenic Rapid, Inducible Amyloid Deposition" (TRIAD) mouse model is an extension of the above described AA transgenic mouse model. It is simply a model in which the initiation of amyloid disease is controllable and rapid, with respect to the untreated model.

1. Materials and Method

Amyloid deposition was initiated by the injection of 100 µl of a 0.1 mg/ml preparation of AEF in sterile water or PBS. The injection was given intravenously in the tail vein of six-week old hIL-6 transgenic mice (described above). AEF may also be administered by intramuscular injection or supplied in the animals' drinking water.

2. Results and Discussion

Figure 5:
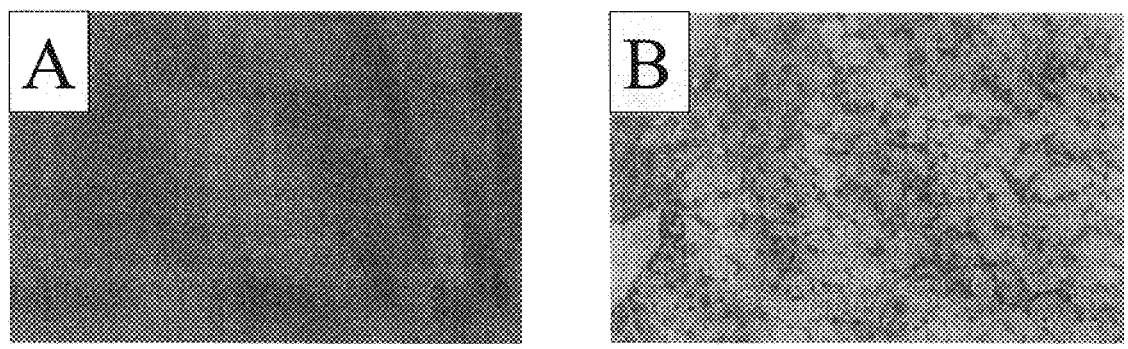
FIGS. 5A and 5B show histological results of hepatic amyloid in a hIL-6 transgenic mouse 6 weeks post-AEF injection. A) Congo red staining of liver section viewed under crosspolarized light. Amyloid is seen as foci (×40). B) Light microscopic image of liver amyloid deposits (×80).
Figure 6:
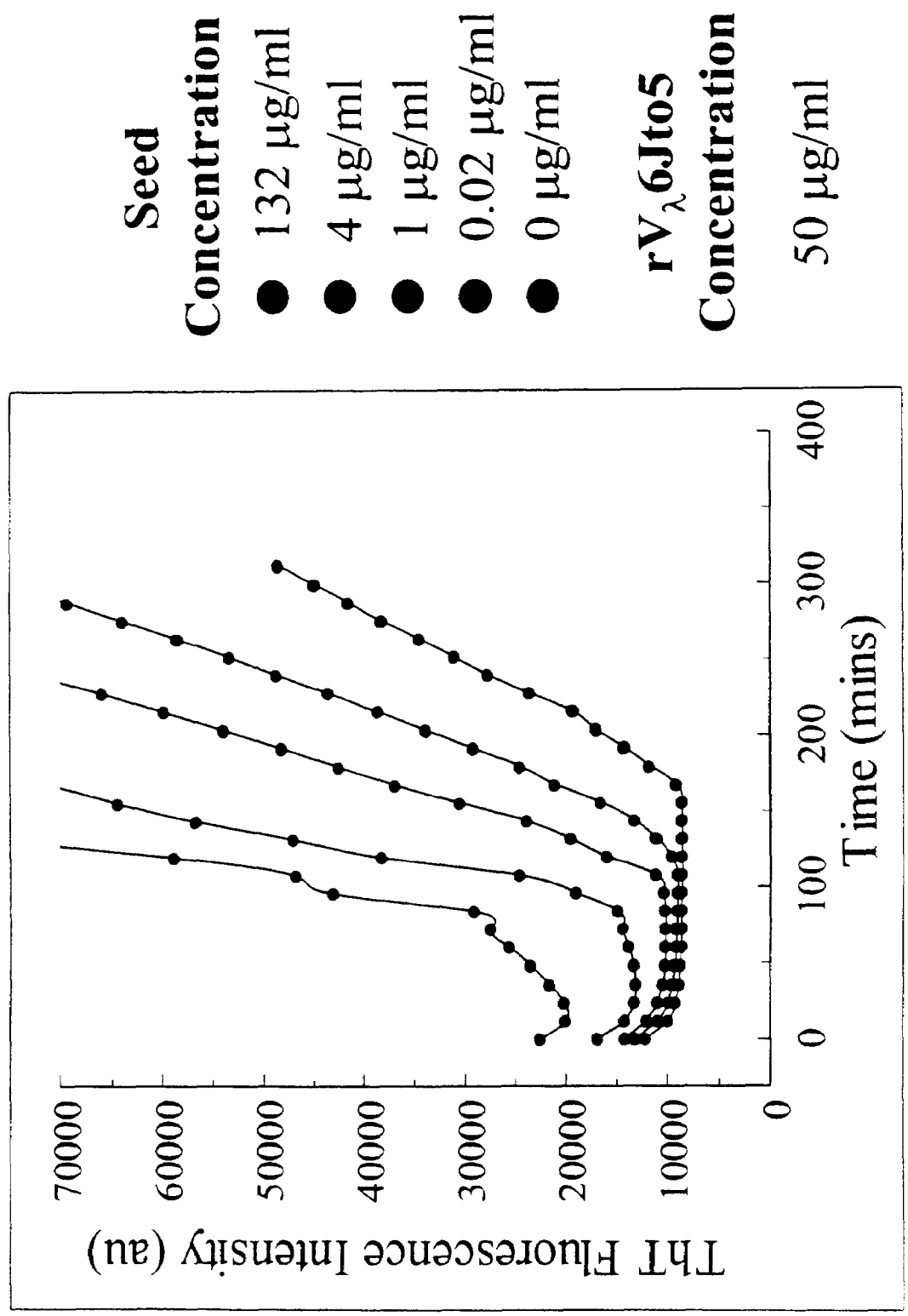
FIG. 6 shows seeding the fibrillogenesis of rV$_\lambda$6Jto5 (recombinant immunoglobulin light chain protein).
Figure 7:
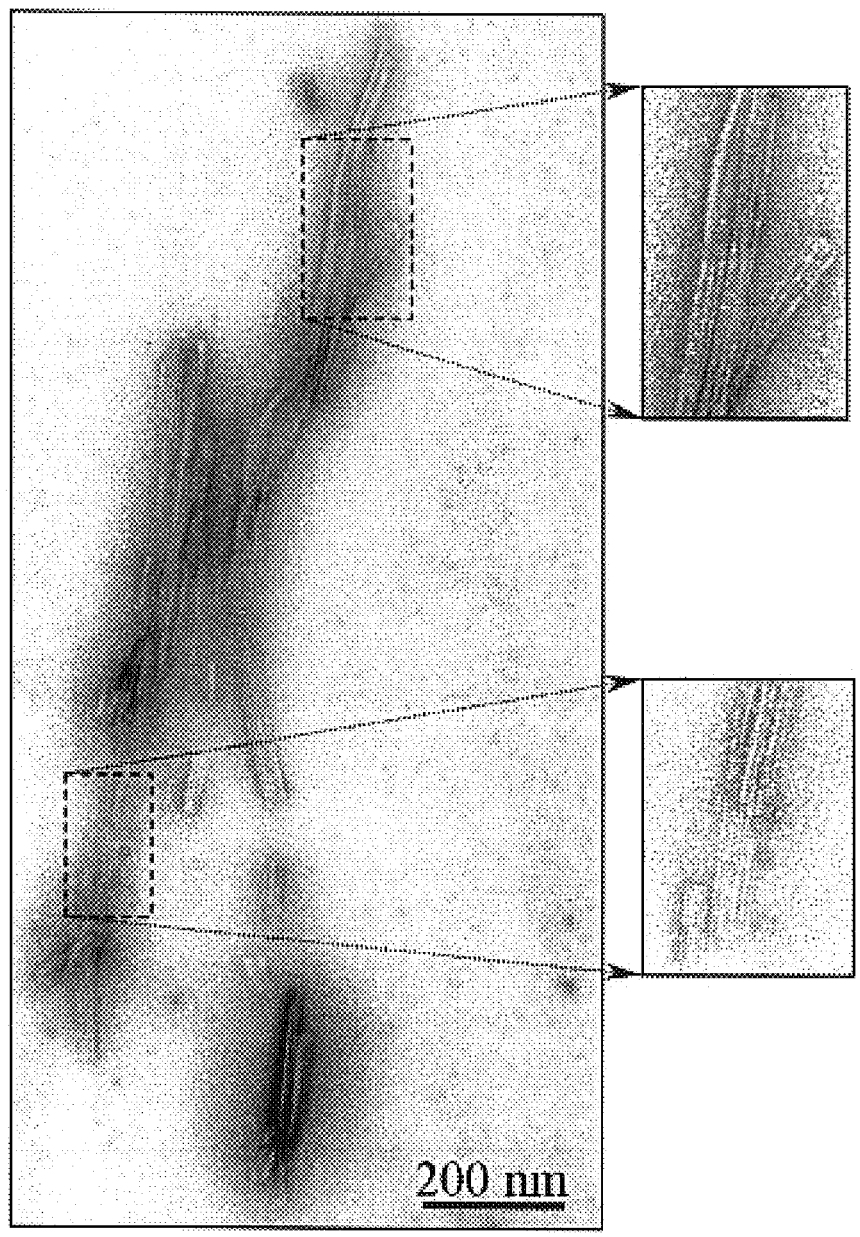
FIG. 7 shows the ultrastructure of rV$_\lambda$6Jto5 fibrils. Fibrils formed by rV$_\lambda$6Jto5 in the microplate assay are ultrastructurally indistinguishable from those formed by other methods. They are characterized by linear unbranching filaments (2-14 nm in diameter) which exhibit increasing orders of structural complexity. The bundles appear to have circular cross-sections as shown in the enlarged images. In contrast to other recombinant V$_\lambda$6 fibrils, no twisting of the filaments is evident.

The TRIAD mouse model is based on the discovery that amyloid deposits can be induced in young, i.e. six-week old mice. FIGS. 5A and 5B show hepatic amyloid in hIL-6 transgenic mouse 6 weeks post-AEF injection. Six-week old mice develop extensive amyloid deposits in the heart and pancreas in addition to the liver, spleen, and kidneys. These pathologic deposits, in contrast to those induced by chemical stimuli are irreversible and lead to death of the animal.

C. Method of Identifying Agents that Prevent or Treat Amyloidosis Using the Transgenic or TRIAD Mouse 1. Materials and Methods Procedure for preparation of immunoglobulin light chain polypeptide and immunization of mice are described in Schenk et al. (1999).

Immunoglobulin light chain polypeptide (test agent) is freshly prepared from lyophilized powder for each set of injections. For immunizations, 2 mg of the immunoglobulin light chain polypeptide is added to 0.9 ml deionized water and the mixture is vortexed to generate a relatively uniform suspension. A 100 µl aliquot of 10× PBS (where 1×PBS is 0.15 M NaCl, 0.01 M sodium phosphate, pH 7.5) is added. The suspension is vortexed again and incubated overnight at 37° C. for use the next day.

Immunoglobulin light chain polypeptide is emulsified 1:1 (v/v) with complete Freund's adjuvant for the first immunization of six week old transgenic MT-1/hIL-6 mice, followed by a boost in complete Freund's adjuvant at 2 weeks, and monthly thereafter. For control, PBS is emulsified with complete Freund's adjuvant and administered to six week old transgenic MT-1/hIL-6 mice as the first immunization, and is followed by a boost in complete Freund's adjuvant at 2 weeks, and monthly thereafter.

MRI and CT are performed, as described in Section A above, to follow the development of amyloid deposits in the mice.

The life span of the animals are compared to determine whether the immunoglobulin light chain polypeptide is effective in preventing AA amyloidosis by increases the life of the transgenic animal.

2. Discussion

The above screening assay may be modified for identifying agents effective in preventing AA amyloidosis using TRIAD mice described in Section B to identify agents effective in preventing AA amyloidosis. AEF and the test agent are administered to young (six week old) transgenic MT-1/hIL-6 mice.

As another embodiment, the assay may be modified for identifying agents effective in treating AA amyloidosis using either MT-1/hIL-6 transgenic mice or TRIAD mice. The test agent is administered after the MT-1/hIL-6 transgenic mice develop amyloid deposits. The test agent is administered three weeks after AEF is administered to a six week old transgenic mice.

The above screening assay may be modified using other transgenic animals and other test agents. It is within the skill of the artisan given the specification and the example above to determine the appropriate amount of test agent to administer to the transgenic animal.

D. Synthetic Amyloid Fibrils for Removal of In Vivo Amyloid Fibrils

1. Immunization Protocol

Synthetic fibrils composed of recombinant immunoglobulin light chain variable-region domains were synthesized as described in Wall et al. (1999). The fibril preparations were washed three times by centrifuigation at 10,000×g for 5 minutes in sterile PBS and resuspended after the final wash at a concentration of 5 mg/ml in sterile PBS. The fibrils were mixed with adjuvant (either Ribi or ALUM) at the appropriate ratio (e.g., 1:1 (v:v) with ALUM adjuvant) to yield a final concentration of 1 mg/ml fibrils.

The first immunization injection was given on day zero. A 100 µl volume of immunogen in adjuvant was injected i.p. Control animals received 100 µl of vehicle solution (ALUM and PBS without fibrils). The mice then received further injections on the following days:

| | | |
|---|---|---|
| 2nd immunization | Day 7 | 100 µl injection i.p. |
| 3rd immunization | Day 14 | 100 µl injection i.p. |
| 1st boost | Day 35 | 100 µl injection i.p. |
| 2nd boost | Day 56 | 100 µl injection i.p. |

The mice were bled on days 15 and 36, and the presence of antifibril antibodies in the serum was determined using an ELISA type assay. The animals were induced to develop AL-amyloidoma or systemic AA-amyloidosis. The AL-amyloidoma was induced by subcutaneously injecting between 70-200 mg of isolated human AL amyloid extract, between the scapulae, on day 59. The AA amyloidosis can be induced by i.v. injection of 100 µl of AEF on day.

The injection of human AL amyloid extract induced the development of a huge lump which is the amyloidoma and can be seen and felt. The amyloid removal was monitored by palpating the AL-amyloidoma. By day 5, the lump disappeared indicating that the amyloid was removed.

2. Disucussion

It is believed that fibrils are structurally homologous at the ultrastructural level, irrespective of the precursor protein from which they are formed. Accordingly, immunization of mice with synthetic fibrils will produce a polyclonal immune response with antibodies which recognize these similar structural motifs. Thus, immunizing a subject with any synthetic fibril preparation will generate antibodies that recognize and effectively remove many types of amyloids (homologous or heterologous). For example, the antibodies raised against synthetic light chain fibrils will react with TTR (transthyretin), β/A4 (Alzheimer's peptide), AA (serum amyloid A protein), ApoAI, and lysozyme amyloid deposits, due to the occurrence of common structural motifs. The method above may be modified for immunization with other synthetic amyloid fibrils composed of purified proteins or peptides.

Synthetic amyloid fibrils are potentially useful as vaccines for the treatment and prevention of primary (AL) amyloidosis as well as other types of amyloid-associated disorders, e.g. adult onset (type 2) diabetes and Alzheimer's Disease.

E. Chemical Identification of Amyloid Using Ultra-Thin Sections of Formalin-Fixed, Paraffin-Embedded Tissue Sections

Materials and Methods

Sample Preparation from Microscopic Slides

Microscopic slides (n 15-20) were washed in Americlear (Baxter) for 48-65 hr under a hood. The slides were rehydrated in a descending series from 100% ethanol, 95% ethanol/water, 80% ethanol water to distilled water each for 5 minutes. Excess water was drained off with a paper towel and the slides were dried in a cover slide rack in a plastic box until they are completely dry. The tissue samples were loosened on one edge with a razor blade and scraped off from the slides with a small scalpel (Feather #11 for #3) into an Eppendorf tube (content 1.8 ml). To the collected tissue samples, 200 µl of 0.25 mol Tris-HCl (pH 8.0) with 1 mmol Na-EDTA and 800 µl of 8M guanidine hydrochloride solution (Pierce) was added. The samples were incubated at 37° C. until all or nearly all the material was dissolved. Samples that did not easily dissolve were sonicated several times. For reduction of the disulfide bonds 30 µl of 2-mercaptoethanol (Pierce) was added and incubated after short vortexing at 37° C. for 2hr. Subsequently, 30 µl of 4-vinylpyridine were added to the solution for at least 30 minutes at 37° C. for alkylation of the sulfhydryl groups.

Separation of the Proteins by HPLC and Tryptic Digestion

The supernatant from the extraction was freed of particulate material by centrifugation at 10,000 rpm. The clear solution was injected onto a Brownlee Aquapore RP-300 $C_8$ column (30×4.6 mm). The components of the solution were separated by a linear gradient from 0.1% trifluoroacetic acid in water/10% acetonitrile to 0.1% trifluoroacetic acid in water/70% acetonitrile in 45 minutes by a model 140A solvent delivery system (Applied Biosystems, Foster City, Calif.) with a flow rate of 1 ml/min. The absorbancy was read at 220 nm. Fractions were collected manually. The collected fractions were dried in a Speed Vac sample concentrator (Savant Instruments, Farmingdale, N.Y.). The fractions were reconstituted with 100 µl of 0.1 M N-methylmorpholine/acetate buffer (pH 8.0). Trypsin (Promega) dissolved in the same buffer was added in an estimated ratio of 1:20 to 1:50. The digestion mixture was incubated at 37° C. for 2 to 4 hr. Subsequently, the sample was concentrated to about 25 µl with the "SpeedVac" sample concentrator.

Mapping of the Tryptic Peptides and Amino Acid Sequence Determination

Tryptic peptides generated from different proteins were separated on microbore columns (150×0.5 mm) filled with Aquabore 300 $C_{18}$ reverse phase (Perkin Elmer, Brownlee Column) using a Model 140 D solvent delivery system, a model 785 A programmable absorbance detector, and a model 112 A injector (all from PE Applied Biosystems). The microbore column was eluted with a gradient from 0.1% trifluoroacetic acid/water/5% acetonitrile linearly increasing to 15% acetonitrile within 10 min., followed by a shallower rise to 35% acetonitrile within 125 min, and finally a steeper climb up to 70% acetonitrile within 40 min. Pure acetonitrile was used as solvent B, to which 0.85% trifluoroacetic acid was added to compensate for differences in transmittance. The absorbance was read at 215 nm and recorded on a strip chart recorder (Kipp & Zonen) at a speed of 1 mm/min. The flow rate was 5 µl per minute. Eluted peptides were spotted on a PVDF membrane by a model 173A microblotter (PE Applied Biosystems). Guided by the elution diagram recorded on the chart recorder, peptide containing spots were cut off the PVDF membrane and placed in the plot cartridge of a Procise automatic amino acid sequencer (PE Applied Biosystems). The amino acid sequencer was ran according to a protocol supplied by the manufacturer.

F. In Vitro Microplate Assay to Identify Compounds that Inhibit Immunoglobulin Light Chain Fibrillogenesis There are essentially two versions of the microplate assay, "Unseeded" and "Seeded". The former is performed using a 48-well microplate, and the latter in a 96-well plate but may also be performed using the new 384-well plates. Jto5 is the name of a recombinant immunoglobulin light chain protein, which was used as the substrate for the assay, although any fibrillogenic protein may be used. The assay uses fluorescence in a multi-well format as well as fluorescent dye ThT in the reaction mixture from the offset. This latter point circumvents the need to sample the reaction mixture and provides a real time measurement of fibrillogenesis.

The assays described below are for determining whether a test agent or compound inhibits fibrillogenesis. The assays can be modified to monitor the fibrillogenesis of a compound. In which case, the test agent or compound to be tested is omitted from the assays.

Materials and Methods

Stock solution of Jto5 was prepared by hydrating the protein at >2 mg/ml in PBS and filtering the solution through a 0.2 μm pore-sized filter (Acrodisc). The concentration of the protein was calculated using the $\in_{280}$ of 12,253. The working solution of Jto5 was 50 μg/ml in PBS with 10 μM ThT.

ASSAY#1: Unseeded.

Seven hundred and fifty microliter of Jto5 working solution was aliquoted into every well of a Falcon 48-well microplate. Compounds were tested at 0.4×, 0.04×, and 0.004× molar equivalents (i.e., 50 μg/ml Jto5=4 μM, therefore, compounds are used at 1 μM, 0.1 μM, and 0.01 μM). Working dilutions of compounds were prepared in DMSO at 251× the required final concentration in the well, such that the addition of 3 μl of compound to 750 μl yielded the correct final concentration. Compound was added to wells in duplicate. Three μl of DMSO alone was added as a control, and a minimum of three wells were left without DMSO or compound as a second control.

Fibrillogenesis was performed in Bio-Tek FL600 fluorescence plate reader at 40° C.±0.5° C. using the appropriate 495 nm cut off filter for the emission and a 435 nm excitation filter. The plate was shaken for three minutes prior to each reading. Kinetic readings were made every 10 minutes.

ASSAY #2: Seeded.

One hundred and fifty microliter of Jto5 working solution was aliquoted into every well of a Costar clear-bottom white 96-well microplate. Three microliter of seed solution (about 0.075 mg/ml sonicated Jto5 fibrils) was added to every well. Compounds were tested at 0.4×, 0.04×, and 0.004× molar equivalents (i.e., 50 μg/ml Jto5=4 μM, therefore, compounds were used at 1 μM, 0.1 μM, and 0.01 μM). Working dilutions of compounds were prepared in DMSO at 153× the required final concentration in the well, such that the addition of 1 μl of compound to 150 μl yielded the correct final concentration. Compound was added to wells in duplicate. One microliter of DMSO alone was added as a control. A minimum of 3 wells was left without DMSO or compound as a second control.

Fibrillogenesis was performed in Bio-Tek FL600 fluorescence plate reader at 40° C.±0.50° C. using the appropriate 495 nm cut off filter for the emission and an 435 nm excitation filter. The plate was shaken for three minutes prior to each reading. Kinetic readings were made every 10 minutes.

It should be understood that the foregoing discussion and examples merely present a detailed description of certain preferred embodiments. It therefore should be apparent to those of ordinary skill in the art that various modifications and equivalents can be made without departing from the spirit and scope of the invention. All journal articles, other references, patents and patent applications that are identified in this patent application are incorporated by reference in their entirety.

REFERENCES

The following references are herein incorporated by reference in their entirety:

Austin et al., J Biol Chem (1996) 271(7): 3737-3742.
Bellotti et al., Scand. J. Immunol: (1992) 36(4):607-615.
Bellotti et al., Ren. Fail. (1993) 15(3):365-371.
Bickel et al., Bioconjug. Chem. (1994) 5(2):119-125.
Brandt et al., J Clin Invest (1990) 86:592-599.
Bronson et al., Proc Natl Acad Sci USA (1996) 93(17): 9067-9072.
Carroll et al., Cell (1995) 83(6): 957-68.
Carroll et al., J Invest Dermatol (1997) 108 (4): 412-422.
Cicatiello et al, Mol Endocrinol, (1995) 9: 1077-1090.
Eulitz et al., Proc Natl Acad Sci USA (1996) 87:6542-6546.
Fattori et al, Blood (1994) 83:2570-2579.
Fattori et al., J Exp Med (1994) 180:1243-1250.
Feng et al. Genes Dev (1997), 11 (1): 59-71.
Foyn et al., Scand J Innunol (1994) 40:337-344.
Furth et al., Proc Natl Acad Sci. (1994) 91(20): 9302-9306.
Galou et al., Glia (1994) 12(4): 281-293.
Gillmore et al., Brit J Haematol (1997) 99:245-256.
Gloster et al., J Neurosci (1994)14(12): 7319-30.
Hirano et al., Immunol Today (1990)11:443-449.
Hogan et al., "Manipulating the Mouse Embryo: A Laboratory Manual", Cold Spring Harbor Laboratory, Cold Spring Harbor, N.Y., USA, 1986.
Hsu-Wong et al., J Biol Chem (1994) 269(27): 18072-18075.
Husby et al., Amyloid Int J Exp Clin Invest (1994) 1:119-137.
Husebekk et al., Scand J Immunol (1985) 21:282-287.
Johnson et al. Proc. Natl. Acad. Sci. U.S.A. (1985) 82 (7): 1896-1900.
Kishimoto et al., Annu Rev Immunol (1988) 6:485-512.
Kisilevsky et al., Pathogenesis of Amyloidosis. Bailliere's Clinical Rheumatology: Reactive Amyloidosis and the Acute-Phase Response. (1994) Vol 8, No 3, 613-626.
Le, Lab Invest (1989) 61:588-602.
Lee et al., Int J Dev Biol (1995) 39(3): 469-75.
Lee et al., J Biol Chem (1996) 271(8): 4561-8.
McGlynn et al., Mol Cell Biol (United States) (1996) 16(5):1936-45.
Meek et al, J Exp Med (1986) 163:499-510.
Mendelsohn et al., Mech Dev (1994) 45(3): 227-241.
Missero et al., J Cell Biol (1993) 121 (5): 1109-1120
Nordstoga et al., Zentralbl Veterinarmed A (1994) 41: 741-747.
Pras et al., J Clin Invest (1968) 47:924-933.
Prelli et al., Scand J Immunol (1991) 33:783-7866.
Ray et al., Mol Cell Biol (1996) 16(5): 2056-64.
Rincon-Limas et al., J Neurosci Res (1994) 38(3): 259-67.
Sim et al., Cell (1979) 18:1303-1316.
Sipe, Crit Rev Clin Lab Sci (1994) 31:325-354.

Sipe, Annu Rev Biochem (1992) 61:947-975.
Skinner et al., Lab Invest (1997) 36:420-427.
Solomon et al., American Journal of Pathology (1999) 154:1267-1272.
Solomon et al., Am J Pathol (1990) 137:855-862.
Suematsu et al., Proc Natl Acad Sci USA (1989) 86: 7547-7551.
Tape et al., Scand J Immunol (1988) 28:317-324.
Van Snick, Annu Rev Immunol (1990) 8:253-257.
Vicart et al., Exp Cell Res (1994) 214(1): 35-45.
Walker et al., J. Neuropathol. Exp. Neurol. (1994) 53(4): 377-383.
Wall et al., Meths. Enzymol. (1999) 309, 204-217.
Wang et a!L Proc Natl Acad Sci USA (1997) 94 (1): 219-226.
Woodroofe et al., DNA Cell Biol (1992) 11:587-592.
Yang et al., Cell Growth Differ (1996) 7(9): 1227-37.
Yoneda et al., Proc Natl Acad Sci USA (1993) 90 (22): 10754-10758.

The invention claimed is:

1. A method of removing amyloid deposits from a subject comprising administering to the subject amyloid fibrils comprising an immunoglobulin light chain polypeptide or a whole immunoglobulin light chain polypeptide, heterologous to the amyloid fibrils in the subject, in an effective amount to generate an immune response, wherein the immune response promotes the removal of amyloid deposits from the subject.

2. A method of claim 1, wherein the amyloid fibrils are synthetic amyloid fibrils.

3. A method of claim 2, wherein the synthetic amyloid fibrils comprise recombinant protein or polypeptide.

4. A method of claim 2, wherein the synthetic amyloid fibrils comprise purified native protein or polypeptide.

5. A method of claim 1, wherein the amyloid fibrils are recombinant amyloid fibrils.

6. A method of claim 1, wherein the amyloid fibrils are naturally occurring amyloid fibrils.

7. A method of claim 1, wherein the subject is a mammal.

8. A method of claim 7, wherein the mammal is a human.

9. A method of claim 1, wherein about 10% or more of the amyloid deposits are removed as compared to the subject without treatment of amyloid fibrils.

10. A method of claim 9, wherein about 20% or more of the amyloid deposits are removed as compared to the subject without treatment of amyloid fibrils.

11. A method of claim 10, wherein about 30% or more of the amyloid deposits are removed as compared to the subject without treatment of amyloid fibrils.

12. A method of claim 11, wherein about 40% or more of the amyloid deposits are removed as compared to the subject without treatment of amyloid fibrils.

13. A method of claim 12, wherein about 50% or more of the amyloid deposits are removed as compared to the subject without treatment of amyloid fibrils.

14. The method of claim 1, wherein the immunoglobulin light chain polypeptide comprises the variable region.

15. The method of claim 14, wherein the immunoglobulin light chain polypeptide comprises the κ or λ chain.

16. A method of removing amyloid deposits from a subject comprising administering to the subject amyloid fibrils comprising an immunoglobulin light chain polypeptide, heterologous to the amyloid fibrils in the subject, in an effective amount to generate an immune response, wherein the immune response promotes the removal of amyloid deposits from the subject.

17. A method of claim 16, wherein the subject is a mammal.

18. A method of claim 17, wherein the mammal is a human.

19. A method of removing amyloid deposits from a subject comprising administering to the subject amyloid fibrils comprising a whole immunoglobulin light chain polypeptide, heterologous to the amyloid fibrils in the subject, in an effective amount to generate an immune response, wherein the immune response promotes the removal of amyloid deposits from the subject.

* * * * *

SEQUENCE LISTING

```
<160> NUMBER OF SEQ ID NOS: 1

<210> SEQ ID NO 1
<211> LENGTH: 58
<212> TYPE: PRT
<213> ORGANISM: Mus musculus

<400> SEQUENCE: 1

Gly Phe Phe Ser Phe Ile Gly Glu Ala Phe Gln Gly Ala Gly Asp Met
1               5                   10                  15

Trp Arg Ala Tyr Thr Asp Met Lys Glu Ala Gly Trp Lys Asp Gly Asp
            20                  25                  30

Lys Tyr Phe His Ala Arg Gly Asn Tyr Asp Ala Ala Gln Arg Gly Pro
        35                  40                  45

Gly Gly Val Trp Ala Ala Glu Lys Ile Ser
    50                  55
```